United States Patent
Chin et al.

(10) Patent No.: US 8,747,350 B2
(45) Date of Patent: Jun. 10, 2014

(54) STEERABLE CATHETER WITH RAPID EXCHANGE LUMEN

(75) Inventors: Yem Chin, Burlington, MA (US); John Golden, Norton, MA (US); Paul Scopton, Winchester, MA (US); Robert DeVries, Northborough, MA (US); John O McWeeney, Brighton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 959 days.

(21) Appl. No.: 11/519,576

(22) Filed: Sep. 11, 2006

(65) Prior Publication Data
US 2008/0097293 A1   Apr. 24, 2008

(51) Int. Cl.
*A61M 31/00* (2006.01)
*A61M 29/00* (2006.01)
*A61M 25/00* (2006.01)

(52) U.S. Cl.
USPC ............... 604/95.04; 604/102.01; 604/525; 606/194

(58) Field of Classification Search
USPC .......... 604/95.04, 102.01, 585, 525; 606/194
See application file for complete search history.

(56) References Cited

U.S. PATENT DOCUMENTS

| | | | | |
|---|---|---|---|---|
| 5,437,288 A | * | 8/1995 | Schwartz et al. | 600/585 |
| 5,438,975 A | * | 8/1995 | Miyagi et al. | 600/109 |
| 5,477,856 A | * | 12/1995 | Lundquist | 600/373 |
| 5,531,677 A | * | 7/1996 | Lundquist et al. | 604/22 |
| 5,554,118 A | * | 9/1996 | Jang | 604/102.02 |
| 5,685,868 A | * | 11/1997 | Lundquist | 604/523 |
| 5,947,925 A | * | 9/1999 | Ashiya et al. | 604/164.08 |
| 6,428,489 B1 | * | 8/2002 | Jacobsen et al. | 600/585 |
| 6,450,948 B1 | * | 9/2002 | Matsuura et al. | 600/139 |
| 7,217,246 B1 | * | 5/2007 | Stone | 600/585 |
| 2004/0138744 A1 | * | 7/2004 | Lashinski et al. | 623/2.36 |
| 2004/0153146 A1 | * | 8/2004 | Lashinski et al. | 623/2.36 |
| 2006/0293646 A1 | * | 12/2006 | Whayne et al. | 606/27 |
| 2009/0082723 A1 | * | 3/2009 | Krogh et al. | 604/95.05 |

FOREIGN PATENT DOCUMENTS

| | | |
|---|---|---|
| FR | 2713492 A1 | 6/1995 |
| WO | 0076570 A | 12/2000 |
| WO | 2006009588 A | 1/2006 |

* cited by examiner

*Primary Examiner* — Nicholas Lucchesi
*Assistant Examiner* — Ian Holloway
(74) *Attorney, Agent, or Firm* — Seager, Tufte & Wickhem LLC

(57) ABSTRACT

A medical device for advancement over a guidewire includes a number of lumens therein including a working channel lumen, one or more control wire lumens, and a guidewire lumen. A flexible support within the device includes a number of interlocking elements that resist longitudinal compression, transfer rotational torque, and can bend side to side. The flexible support also includes a slot that is aligned with the guidewire lumen. An outer jacket includes a perforation, slot, slit, or thinned area that is aligned with the slot in the support member and the guidewire lumen in order to allow a device such as a guidewire to be removed from the guidewire lumen and through the support member.

20 Claims, 9 Drawing Sheets

STEERABLE CATHETER WITH RAPID EXCHANGE LUMEN

TECHNICAL FIELD

The disclosure relates to medical devices in general, in particular to steerable devices for use with a guidewire.

BACKGROUND

As an alternative to performing more invasive medical procedures, many physicians are performing examinations and/or therapeutic procedures in vivo with catheters or other devices. Such devices are generally routed from outside the patient to an area of interest through a small opening in the skin or through a body orifice. Such devices often include one or more lumens by which additional tools, medicines, and the like, can be delivered to a site in order to perform a desired task.

In order to route a catheter to its desired location, many procedures require the use of a guidewire. The guidewire is first advanced by the physician to the point of interest and then left in place to serve as a rail over which additional devices can be routed in order to guide them to the desired location. FIG. 1 shows an example of a conventional guidewire 10 and a catheter 20 positioned over the guidewire. In many procedures, it is desirable to leave the guidewire in place while one catheter is exchanged for another. Therefore, the proximal end 12 of the guidewire 10 is fixed while the catheter 20 is removed from the patient. In order to maintain a handle on the proximal end 12 of the guidewire 10, it is necessary that the portion of the guidewire that remains outside the patient be longer than the length of the catheter 20. Therefore, a catheter/guidewire system such as that shown in FIG. 1, requires the use of long guidewires that can be cumbersome to manipulate and can clutter an operating room.

To address the issues associated with changing catheters over long guidewires, many catheters include so-called "rapid exchange" lumens. As shown in FIG. 2, a rapid exchange catheter 30 includes an opening 32 on the sheath of a catheter and a slot 34 that extends along the length of the catheter through which a guidewire 40 can be pulled. To exchange the catheter 30 for another device while maintaining the position of the guidewire 40 in the body, the catheter 30 is stripped off the guidewire 40 by pulling it through the slot 34. A new catheter or device can be routed over the guidewire 40 by inserting the proximal end of the guidewire 40 into an opening of a guidewire lumen at the distal end of the new device and advanced such that the proximal end of the guidewire exits the opening 32. The opening 32 may be positioned towards the proximal end of the catheter or may be located more towards the distal end.

While rapid exchange catheters and devices have been developed for many procedures, they have not been adapted for use with steerable catheters or catheters that are required to transmit torque from the proximal to the distal end of the catheter. Such devices often include a wire braid to increase column strength and transfer rotational torque. However, cutting this braid to allow the removal of the guidewire results in the braid becoming unraveled or frayed in a manner that can compromise the construction and performance of the catheter.

Because steerable devices are becoming increasingly used to navigate through the patient's body, there is a need for a mechanism to incorporate the advantages of a rapid exchange guidewire lumen with devices that are steerable and/or can transmit torque.

SUMMARY

To address the problems discussed above, the present disclosure is directed to a rapid exchange type medical device that can be steered within the body using one or more control wires and/or can transmit torque from the proximal end to the distal end.

In one embodiment, the device is a catheter that includes an outer jacket and a support member positioned therein that resists longitudinal compression and transfers rotational torque from the proximal end of the catheter to the distal end. In one embodiment, the support member has a number of aligned rings that are joined together with hinges. In addition, the support member includes a longitudinally extending slot along a portion of the circumference of the rings. The slot in the support member is aligned with a guidewire lumen in the catheter and a corresponding slot, perforation, or other opening in the outer jacket through which a guidewire can be removed.

DETAILED DESCRIPTION

Figure 1:
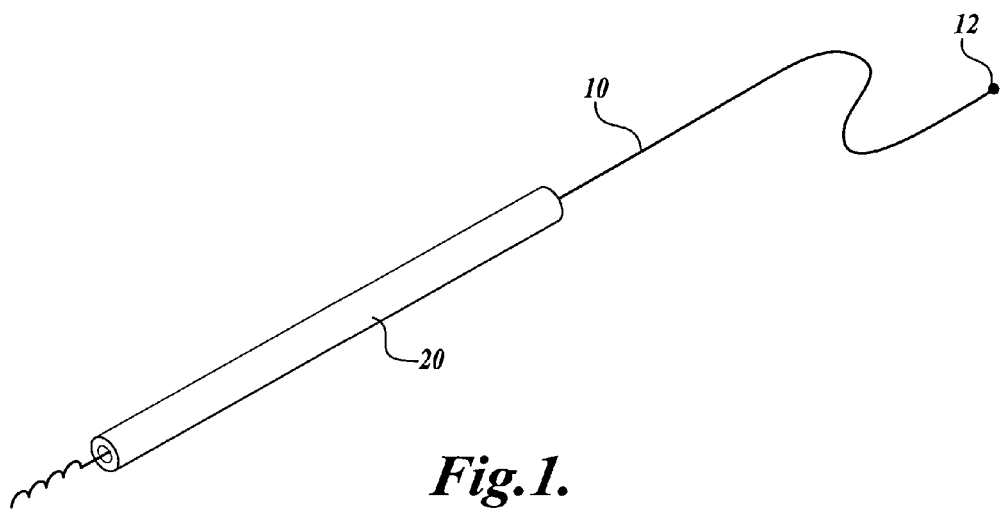
FIG. 1 illustrates a conventional catheter and guidewire.
Figure 2:
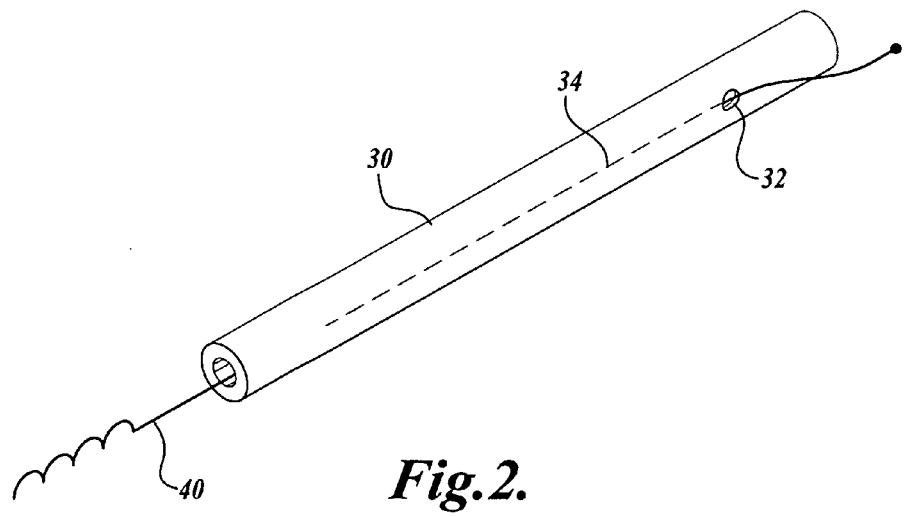
FIG. 2 illustrates a rapid exchange type catheter and guidewire.
Figure 3:
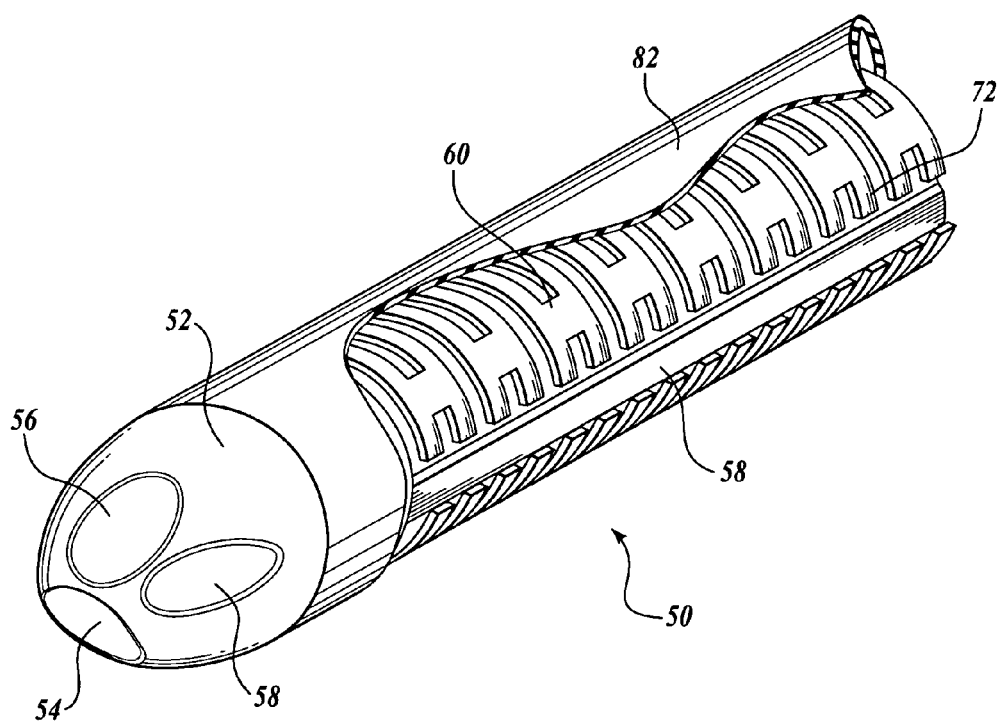
FIG. 3 illustrates one embodiment of a rapid exchange medical device.

As will be described in further detail below, the present disclosure is directed to a rapid exchange catheter or other medical device that can be steered within a patient and/or can transmit rotational torque along its length. Although the embodiments disclosed are configured as catheters, it will be appreciated that the device is useful in any medical instrument that is designed to be used with a guidewire or other tool to be removed from an outer sheath. FIG. 3 illustrates one embodiment of a steerable catheter including a rapid exchange guidewire lumen. The catheter 50 has a distal tip 52 with openings to a number of lumens within the catheter. In the example shown, the distal tip 52 includes an opening 54 to a working channel lumen and an opening 56 to a second lumen, which may be used to route a fiber optic bundle or other tool within the catheter. In addition, the distal tip includes an opening to a guidewire lumen 58 that allows the rapid exchange of the catheter 50 over a guidewire as will be explained in further detail below.

Figure 4:
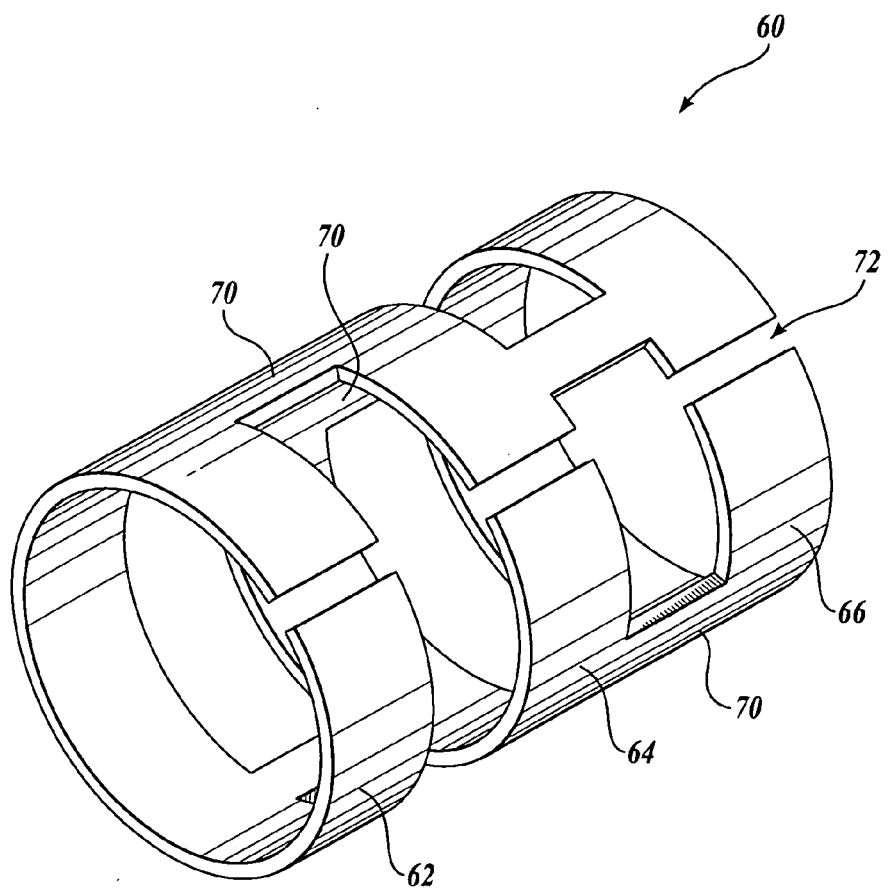
FIG. 4 illustrates one embodiment of a flexible support.

As better shown in FIG. 4, a flexible support 60 extends from the distal tip 52 towards the proximal end of the catheter 50. The flexible support 60 serves to increase the column strength of the catheter 50 and to transfer torque along its length. In one embodiment, the flexible support 60 has a number of axially aligned rings 62, 64, 66, etc., each having an outer edge that extends substantially around the circumference of the catheter 50. Adjacent rings, for example, ring 62 and ring 64, are secured to one another by one or more hinges 70. Between each adjacent pair of rings, the hinges 70 are staggered. For example, in one embodiment, a pair of rings may be secured together with four hinges positioned at 0°, 90°, 180°, and 270° around the circumference of the rings. An adjacent pair of rings may be secured together with hinges positioned at 45°, 135°, 225°, 315°, etc. It will be appreciated that fewer or more hinges could be used to join adjacent rings. For example, each ring could be joined to an adjacent ring with two hinges whereby the hinges are adjacent rings are offset by 90°.

In addition, the flexible support 60 includes a longitudinally extending slot 72 formed by a gap in each of the rings and extending along the length of the support. The slot 72 is aligned with the guidewire lumen 58 within the catheter. As shown in FIG. 3, an outer jacket 82 may cover the flexible member 60. The outer jacket 82 may be made from or coated with a lubricious material, such as PTFE, to facilitate passage of the catheter within a patient's body.

The outer jacket 82 preferably includes a slit, perforation, slot or the like positioned over the area of the longitudinally extending slot 72 in the flexible support 60 and the guidewire lumen 58. In this manner, a guidewire that is positioned within the guidewire lumen 58 can be pulled through the outer jacket 82 and the slot 72 within the flexible support 60 in order to peel the catheter 50 off the guidewire.

The flexible support 60 may be made from a hypotube made from a material such as stainless steel, wherein the rings and hinges are cut with a laser, chemically etched, or ground into the hypotube. Alternatively, the support member 60 can be molded from plastic or other suitable materials.

Figure 5A:
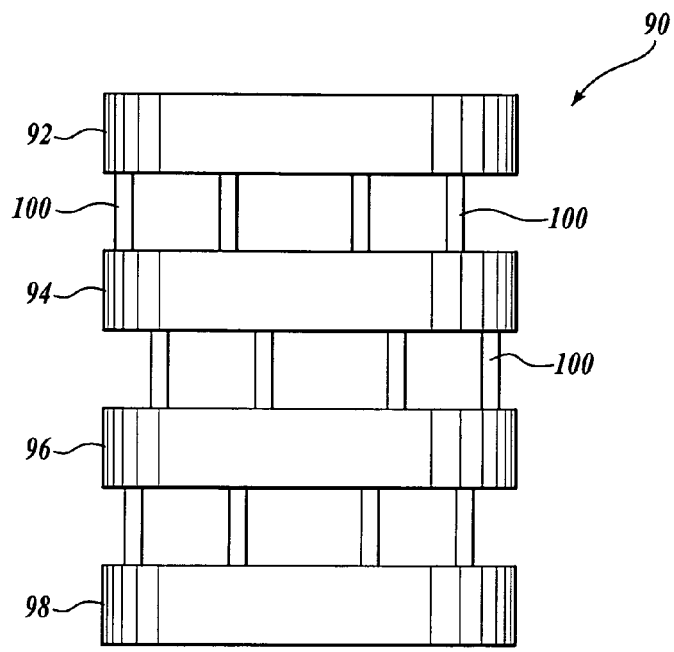
FIGS. 5A and 5B illustrate the flexible supports made from flat sheets of material.
Figure 5B:
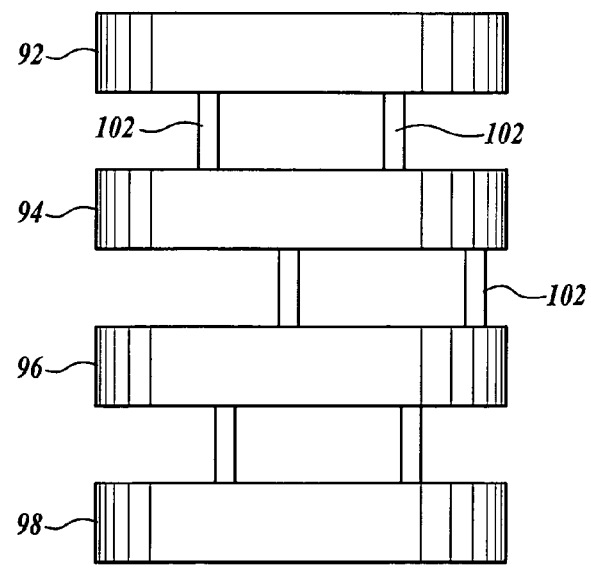

As an alternative to making the support member 60 out of a hypotube, the support member 60 can be made from a flat sheet of material such as stainless steel and rolled or formed into a final shape. As shown in FIG. 5A, a flexible support 90 includes a number of band elements 92, 94, 96, 98 that are joined with hinges 100 extending generally perpendicular to the length of the bands. In the embodiment shown, the hinges 100 between adjacent pairs of bands are staggered or offset from each other. The flexible support 90 can be stamped, molded, etched, or laser cut from a piece of flat material before being rolled or formed into a final shape. Although the bands are shown as being joined together with four hinges in the embodiment shown in FIG. 5A, this is not required. FIG. 5B illustrates an embodiment wherein adjacent bands are joined together with two hinges 102. Each pair of hinges 102 is offset, for example, by 90 degrees, with respect to an adjacent pair of hinges. Once rolled or formed into a tubular shape, each of the bands 92, 94, 96, 98 become the rings of the flexible support. The opposite edges of the bands can be spaced apart to form the slot that is aligned with the guidewire lumen. Alternatively, the opposite edges can be joined by welding or the like and a new slot cut therein to allow passage of the guidewire.

Figure 5C:
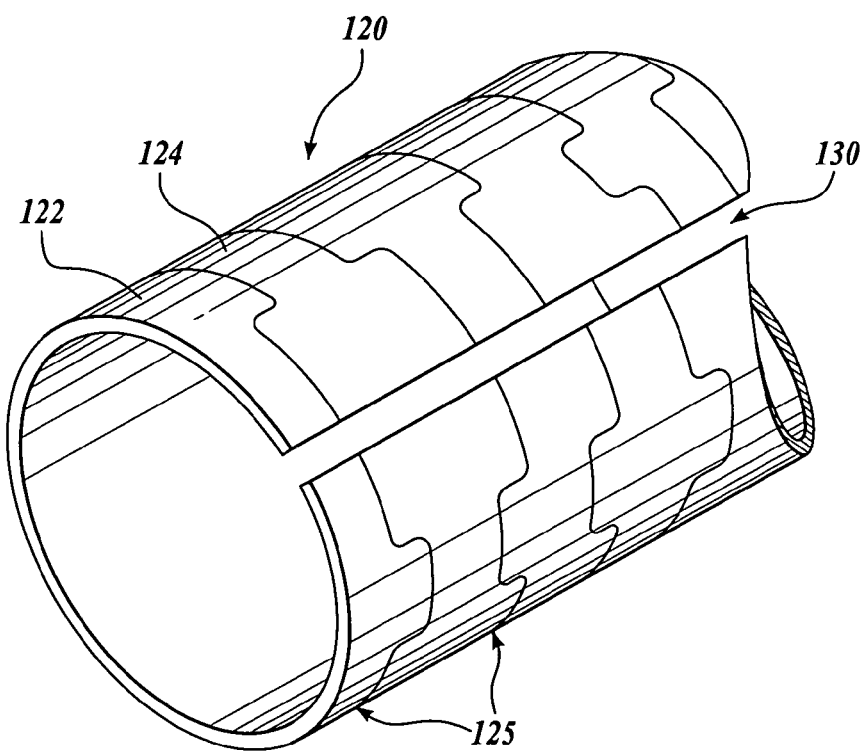
FIG. 5C illustrates another embodiment of a flexible support.

FIG. 5C illustrates yet another embodiment of a flexible support 120. In this embodiment, the support comprises a cylindrical tube having interlocking elements 122, 124, etc., that are joined by a pattern of cuts 125. The flexible support 120 resists compression along its length, but transfers rotational torque when incorporated into the catheter. In addition, the flexible support includes a slot 130 that allows passage of a guidewire out of the guidewire lumen. The flexible support 120 can be made in a manner similar to that used to make medical stents.

Figure 6:
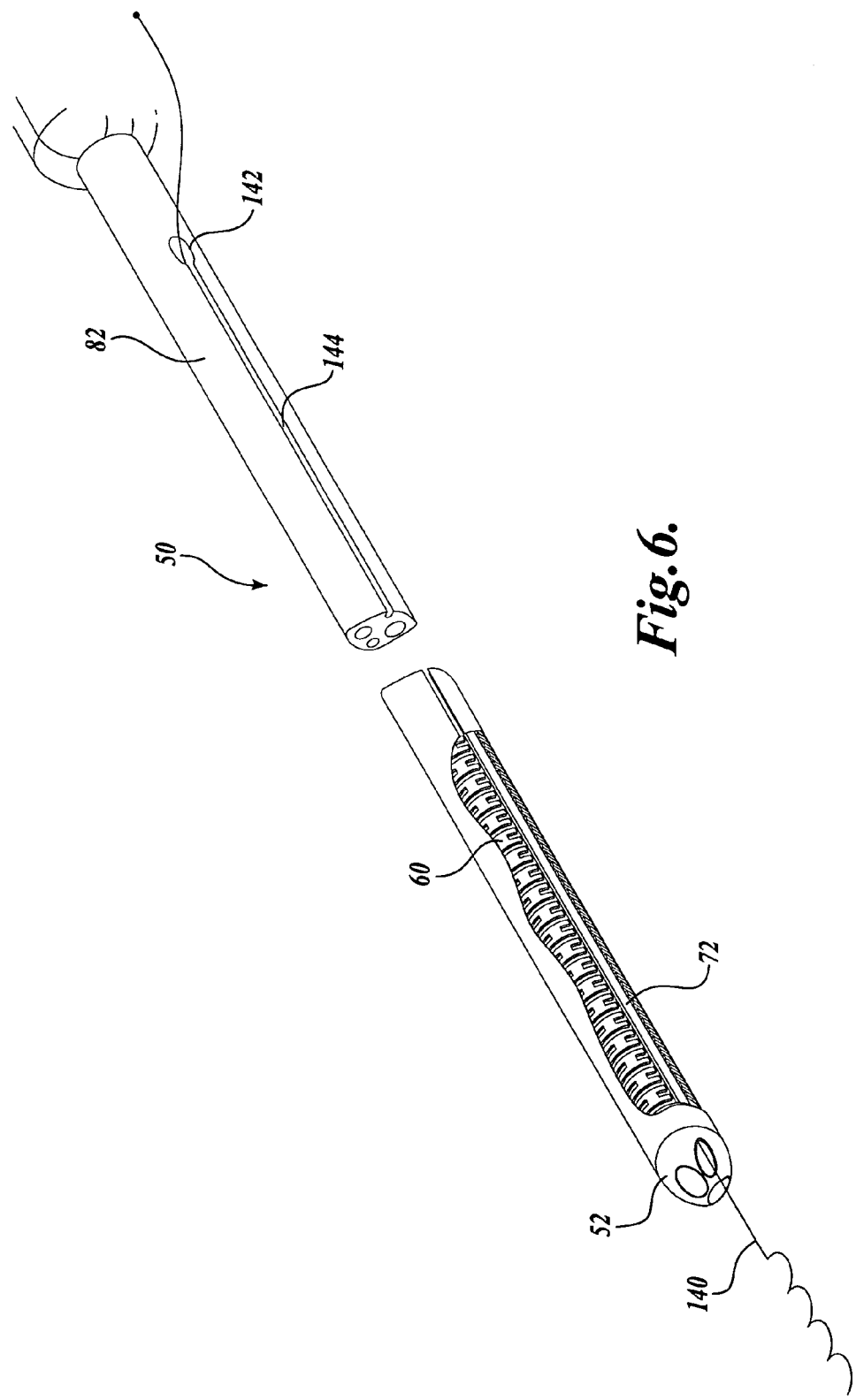
FIG. 6 illustrates a guidewire and a rapid exchange catheter.

FIG. 6 illustrates a catheter 50 routed over a guidewire 140. At the proximal end of the catheter is an opening 142 that allows access to the guidewire lumen within the catheter. A slot 144 extends from the opening 142 towards the distal tip 52 of the catheter and is positioned over the guidewire lumen. In the embodiment shown, the guidewire 140 has a distal end that extends through the opening at the distal end of the guidewire lumen and a proximal end that extends out of the opening 142 in the catheter body. To remove the catheter 50 from the guidewire 140, the guidewire 140 is pulled through the slot 144 extending along the length of the catheter. Because the flexible support 60 has the slot 72 therein, the guidewire can be pulled through outer jacket 82 to exchange the catheter.

Figure 7:
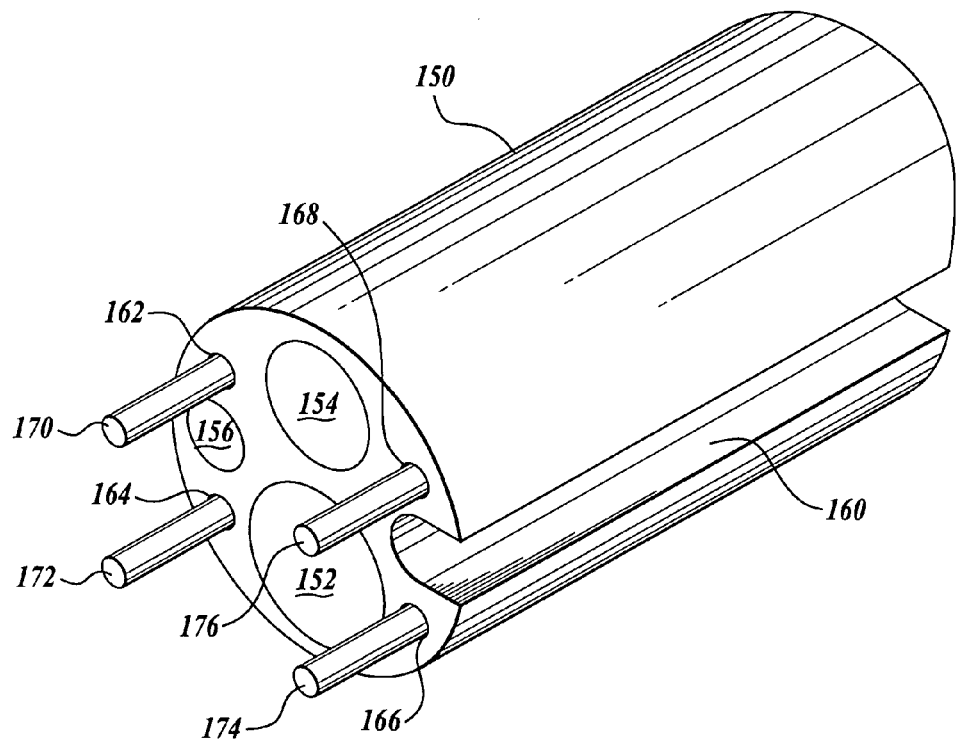
FIG. 7 illustrates a multiple lumen extrusion including a guidewire lumen.

FIG. 7 illustrates one embodiment of an extrusion used to form the various lumens in the catheter. As indicated above, the extrusion 150 may include a working channel lumen 152, a second lumen 154 that can be used to route an optical fiber or other tools through the device. In addition, one or more additional lumens 156 may be provided to pass tools, gases, or liquids through the device. In addition, the extrusion 150 includes a guidewire lumen 160. The guidewire lumen 160 is generally U-shaped such that the lumen has one side open along the circumference of the extrusion 150.

In the example shown in FIG. 7, the extrusion 150 also includes a number of control wire lumens 162, 164, 166, 168 through which corresponding control wires 170, 172, 174, 176 can be routed. Each of the control wires 170-176 has a distal end that is secured at or adjacent the distal end of the catheter and can be selectively tensioned in order to bend the catheter in a desired direction. Although the example shown uses four control wires, it will be appreciated that directional control of the device can be obtained with more or fewer control wires if desired.

In accordance with one embodiment, the flexible support 60 is positioned over the extrusion 150 so that the slot 72 is positioned over the guidewire lumen. The outer jacket 82 is then placed over the flexible member by, for example, an extrusion process or heat reaction, dipping, etc. The flexible support 60, therefore, is sandwiched between the extrusion 150 and the outer jacket 82.

Figure 8A:
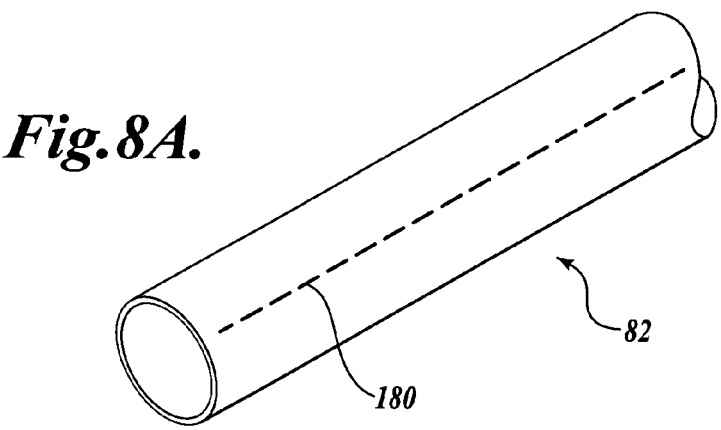
FIGS. 8A, 8B, and 8C illustrate various embodiments of an exterior opening in an outer jacket of a catheter.
Figure 8B:
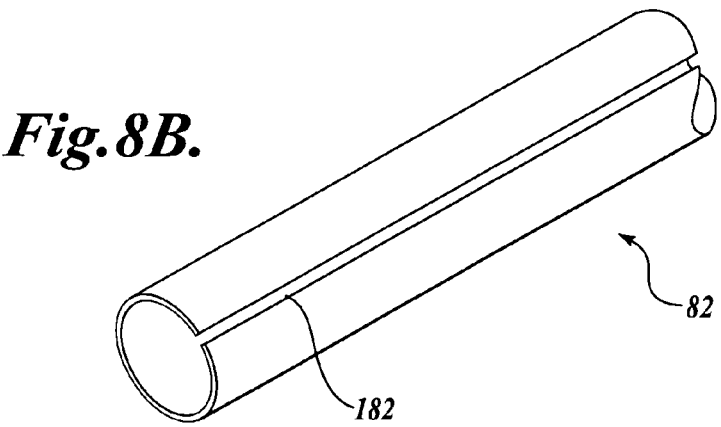
Figure 8C:
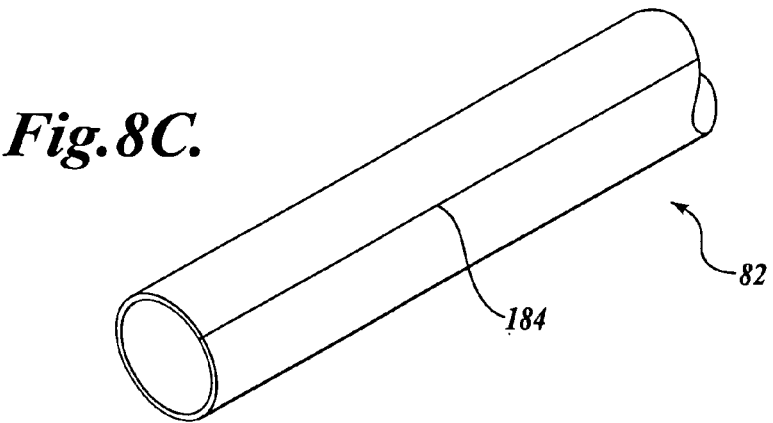

FIGS. 8A-8C illustrate various embodiments of an entrance to the guidewire lumen through the outer jacket 82 of the catheter. In the embodiment shown in FIG. 8A, the entrance comprises a perforated slot 180 extending along the length of the catheter or portion thereof. In the embodiment shown in FIG. 8B, the entrance to the guidewire channel includes a slot 182, wherein the edges of the slot remain some distance apart. In the embodiment shown in FIG. 8C, the entrance to the guidewire channel along the length of the catheter comprises a slit 184 wherein the edges of the slit abut each other. In yet another embodiment, the area over the guidewire channel may be completely sealed by the outer jacket of the catheter. However, the outer jacket may be thin enough in this area such that a guidewire can be pulled through the outer jacket. In yet another embodiment, the outer jacket can be coextruded with a softer material along its length to provide a weaker wall through which a guidewire can be pulled.

Figure 9:
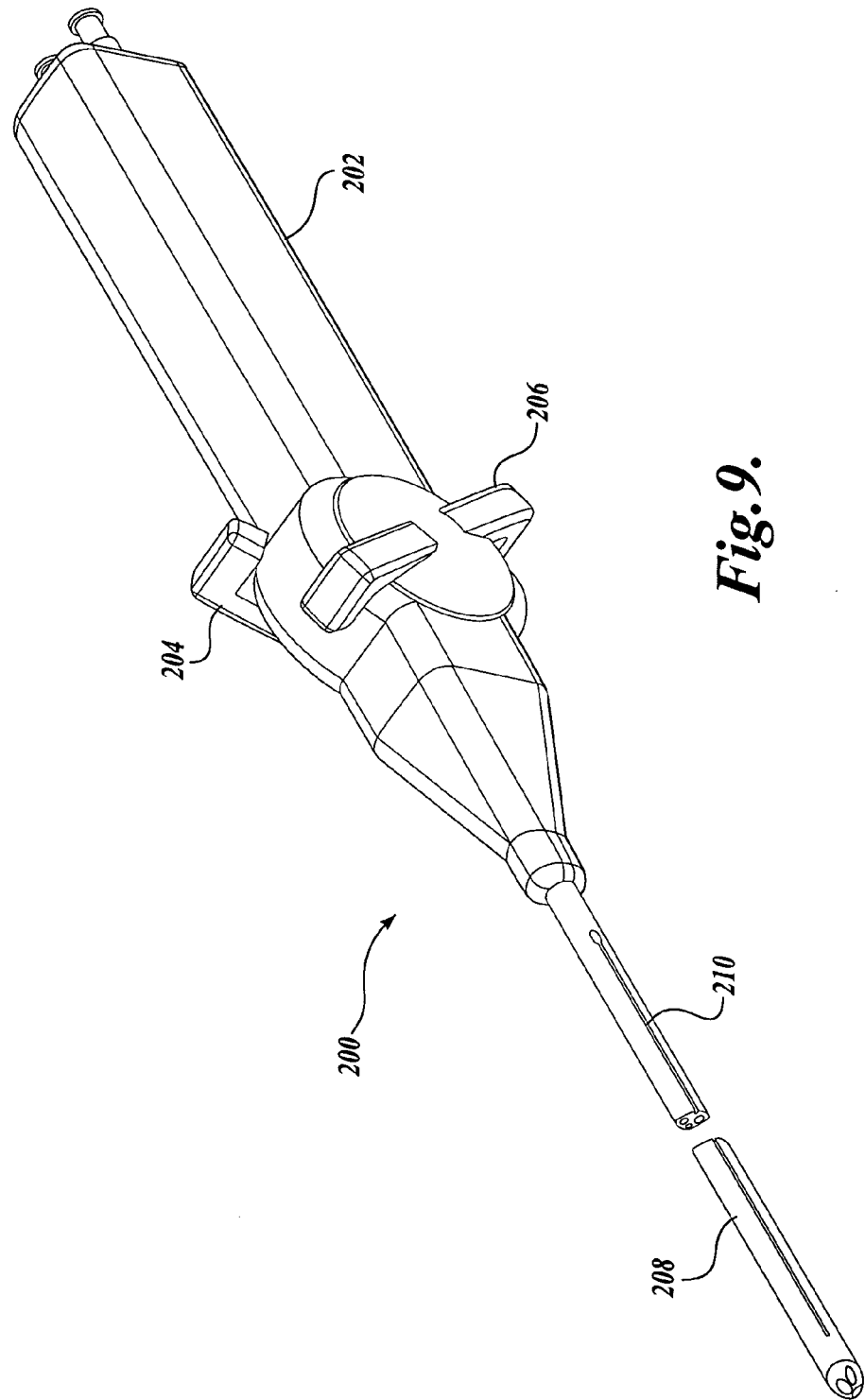
FIG. 9 illustrates one embodiment of a steerable, rapid exchange catheter.

FIG. 9 illustrates one embodiment of a steerable catheter system including a rapid exchange lumen. The catheter 200 includes a handle 202 at a proximal end. The handle 202 has a pair of controls 204, 206 that selectively tension or release pairs of control cables positioned within the catheter in order to steer the distal tip in the desired direction. Extending distally from the handle 202 is a flexible catheter 208, in accordance with any of the above-described embodiments, that is inserted into the patient. The catheter 208 includes a rapid exchange lumen 210 that allows the catheter 208 to be easily removed from a guidewire (not shown) by pulling the guidewire through the side of the rapid exchange lumen 210 in order to exchange the catheter for another one over the guidewire.

While the preferred embodiment of the device has been illustrated and described, it will be appreciated that various changes can be made therein. It is, therefore, intended that the scope of the invention be determined from the following claims and equivalents thereof.

What is claimed is:

1. A medical device comprising:
   a body having a proximal end, a distal end, and a number of lumens therein, the lumens including:
   a working channel lumen;
   at least one control wire lumen;
   a slotted guidewire lumen; and
   a flexible support having a proximal end and a distal end and extending from the distal end of the body toward the proximal end of the body, the flexible support defined by a number of rings that extend circumferentially around the device, hinges that join adjacent pairs of rings together, and a slot extending through the rings and along the flexible support so as to intersect the proximal end of the flexible support, wherein the flexible support slot is aligned with the slotted guidewire lumen such that a guidewire, when extending from a position proximally of the proximal end of flexible support to a position proximally of the distal end of the flexible support, may be removed in a laterally outwardly manner from the slotted guidewire lumen through the flexible support slot;
   wherein the hinges of adjacent pairs of rings are circumferentially staggered about a circumference of the rings.

2. The medical device of claim 1, wherein the body has an outer jacket and the flexible support is positioned between the lumens and the outer jacket.

3. The medical device of claim 2, wherein the lumens are formed in an extrusion positioned within the body, and the flexible support is positioned between the extrusion and the outer jacket.

4. The medical device of claim 2, wherein the outer jacket has a slot aligned with the slot in the flexible support and the guidewire lumen.

5. The medical device of claim 2, wherein the outer jacket has a slit aligned with the slot in the flexible support and the guidewire lumen.

6. The medical device of claim 2, wherein the outer jacket has a reduced thickness in an area over the slot in the flexible support.

7. The medical device of claim 2, wherein the outer jacket includes a softer material in an area over the slot in the flexible support.

8. A medical device, comprising:
   an elongated body having a proximal end, a distal end, a slotted side lumen, and a flexible support having proximal and distal ends, the flexible support extending from the distal end of the body toward the proximal end of the body, wherein the flexible support includes a cylindrical tube including a number of interlocking elements that resist longitudinal compression of the flexible support and transfer rotational torque, the flexible support further including a slot extending along the flexible support and intersecting the proximal end of the flexible support, the slot positioned over the slotted side lumen such that a device can be removed in a laterally outwardly manner from the slotted side lumen through the slot in the flexible support;
   wherein the interlocking elements are shaped such that adjacent elements are in contact with each other.

9. The medical device of claim 8, wherein the elongated body comprises an outer jacket and the flexible support is positioned between the side lumen and the outer jacket.

10. The medical device of claim 9, wherein the outer jacket comprises a slot aligned with the slot in the support member.

11. The medical device of claim 9, wherein the outer jacket comprises a slit aligned with the slot in the support member.

12. The medical device of claim 9, wherein the outer jacket comprises a thin area aligned with the slot in the support member.

13. The medical device of claim 9, wherein the outer jacket comprises a softer material aligned with the slot in the support member.

14. The medical device of claim 8, wherein the side lumen is sized to receive a guidewire therein.

15. The medical device of claim 8, further comprising one or more control wires therein that are selectively tensioned to control the orientation of the distal end.

16. A medical device, comprising:
   (a) an extruded body having a proximal end and a distal end, the extruded body having a plurality of lumens extending therethrough, the plurality of lumens including a steering wire lumen and a guidewire lumen;
   (b) a steering wire extending through the steering wire lumen;
   (c) a flexible support member comprising a number of rings that extend circumferentially around the device and hinges that join adjacent pairs of rings together wherein the hinges of adjacent rings are offset from one another, the flexible support member positioned over the extruded body and extending from the distal end of the extruded body toward the proximal end of the extruded body, the flexible support member configured to increase the column strength of the device and transfer rotational torque along the length of the device; and
   (d) a longitudinal slot formed in the flexible support member and the guidewire lumen so that a guidewire may be removed in a laterally outwardly manner from the guidewire lumen through the slot.

17. The medical device of claim 16, further comprising an outer jacket positioned over the extruded body and the flexible support member.

18. The medical device of claim 17, wherein the outer jacket has a slot aligned with the slot in the flexible support member and the guidewire lumen.

19. The medical device of claim 17, wherein the outer jacket has a slit aligned with the slot in the flexible support member and the guidewire lumen.

20. The medical device of claim 17, wherein the outer jacket has a reduced thickness in an area over the slot in the flexible support member.

* * * * *